United States Patent [19]

Kornfeld

[11] Patent Number: 4,668,866
[45] Date of Patent: May 26, 1987

[54] METHOD OF USING FLIR FOR MOTION ANALYSIS

[75] Inventor: Gertrude H. Kornfeld, Alexandria, Va.

[73] Assignee: The United States of America as represented by the Secretary of the Army, Washington, D.C.

[21] Appl. No.: 793,416

[22] Filed: Oct. 31, 1985

[51] Int. Cl.[4] .......................... H04N 5/33; G06K 9/44
[52] U.S. Cl. ..................................... 250/330; 358/113; 382/6; 382/55
[58] Field of Search ............... 250/330, 334, 333, 332; 358/113; 382/6, 55; 128/664

[56] References Cited

U.S. PATENT DOCUMENTS 4,010,367  3/1977  Suzuki ................................. 250/334
4,218,707  8/1980  Reed et al. ........................... 358/113
4,539,704  9/1985  Pastor .................................... 382/55

OTHER PUBLICATIONS

R. Bowling Barnes, "Thermography of the Human Body" *Science,* vol. 140, No. 3569 (May 24, 1963) pp. 870–877.

*Primary Examiner*—Janice A. Howell
*Assistant Examiner*—Constantine Hannaher
*Attorney, Agent, or Firm*—Max L. Harwell; John E. Holford; Anthony T. Lane

[57] ABSTRACT

A method is provided for recording the motions of a subject while exercising or otherwise engaged in physical activity. A far-infrared detection system is used to record the movements of key positions on the subject to simplify subsequent analysis.

7 Claims, 3 Drawing Figures

METHOD OF USING FLIR FOR MOTION ANALYSIS

The invention described herein may be manufactured, used, and licensed by the U.S. Government for governmental purposes without the payment of any royalties thereon.

BACKGROUND OF THE INVENTION

(1) Field of the Invention

The present invention is concerned with Physical Education. It is particularly applicable to athletes or professionals who require unusual skill or physical ability to successfully perform their job. It relates directly to the study of body motion to achieve better efficiency using photography and like methods.

(2) Description of Prior Art

The use of motion picture photography has greatly aided trainers and physical therapists in improving the physical skills of their subjects. It has become well established that awkward movements of the limbs and other parts of the body not only are generally less efficient, but eventually lead to chronic disorders in the joints, tendons and muscles. While ordinary photography records the required information used in this analysis, it also provides so much extraneous data that interpretation is made difficult.

One technique for simplifying the photographs taken is to prepare the subject by attaching reflectors or lights to significant points of his body such as his shoulders, elbows, knees, feet and hands. When photographed against a dark background using highly controlled lightning, so no overall lighting, the movements of these points are naturally greatly enhanced. The use of special clothing on the subject can also improve these pictures. The photos can be taken with TV cameras and then analyzed with computers which read video type signals. The use of any of the above, however, can so encumber the subject as to make the subsequent analysis useless. They also may be useless in many real environments such as an actual athletic contest or simultaneous testing of a large number of subjects.

SUMMARY OF THE INVENTION

The present invention provides a new method of recording a subject's physical activity using a far infrared viewer such as the FLIR. The output signal from these devices provides more useful data than those using visible or near visible light. The data is also more easily processed to the bare essentials needed for training purposes.

DESCRIPTION OF PREFERRED EMBODIMENTS

The feasibility of using a far-infrared viewer to aid in physical training or therapy was indicated by a study of performance wherein it was noted that the joints of subjects engaged in physical activity stood out clearly in their infrared image. Image intensity in far-infrared is proportional to the temperature of the image source. Apparently the metabolic heat released plus frictional heat builds up quickly in these areas. There may also be a lesser amount of insulation in the joint regions. When viewed against a cool background, i.e. room temperature, with the contrast set high and the sensitivity reduced; the image can be reduced to showing only the joints and their motion. A great advantage of viewing subjects in this manner lies in the fact that the level of visible illumination is of no consequence and thus need not be artifically enhanced with possible detriment to the activity being observed. Infrared light sources and reflectors can be used, but these present obvious drawbacks. Raw images are useful for some purposes, but in general a more graphic image is preferred.

Figure 1:
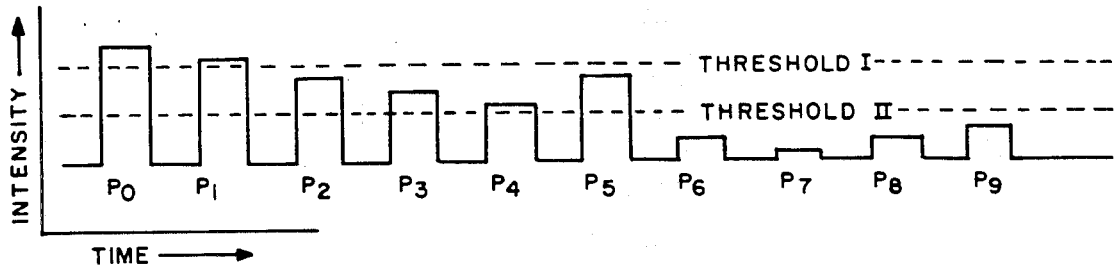
FIG. 1 shows a typical output signal from an infrared viewer.

FIG. 1 shows a representative output signal of the viewer with normal contrast and sensitivity. To interpret the image two abitrary intensity levels designated "THRESHOLD I" and THRESHOLD II are shown. THRESHOLD I represents the lower intensity limit of a group of axial pulses which will be defined that are associated with joints in the human subject's body. THRESHOLD II represents the upper limit of intensity for radial pulses associated with arms, legs, torso, etc. of the same subject between joints. The pulses $P_0$ and $P_9$ could be the output of a sample-and-hold circuit fed by a purely analog signal from a primitive type far-infrared viewer. One early viewer, for example, used two mirrors to scan an infrared image in two dimensions over a small single point detector to produce a TV type video signal. More recent viewers are designed around charge-coupled-devices (CCD'S). These inherently produce such output pulses. They also may have 512 by 512 detector formats which are compatible with the binary and hexadecimal codes found in most computer systems. As in normal TV each detector is sampled at less than one tenth second intervals.

Figure 2:
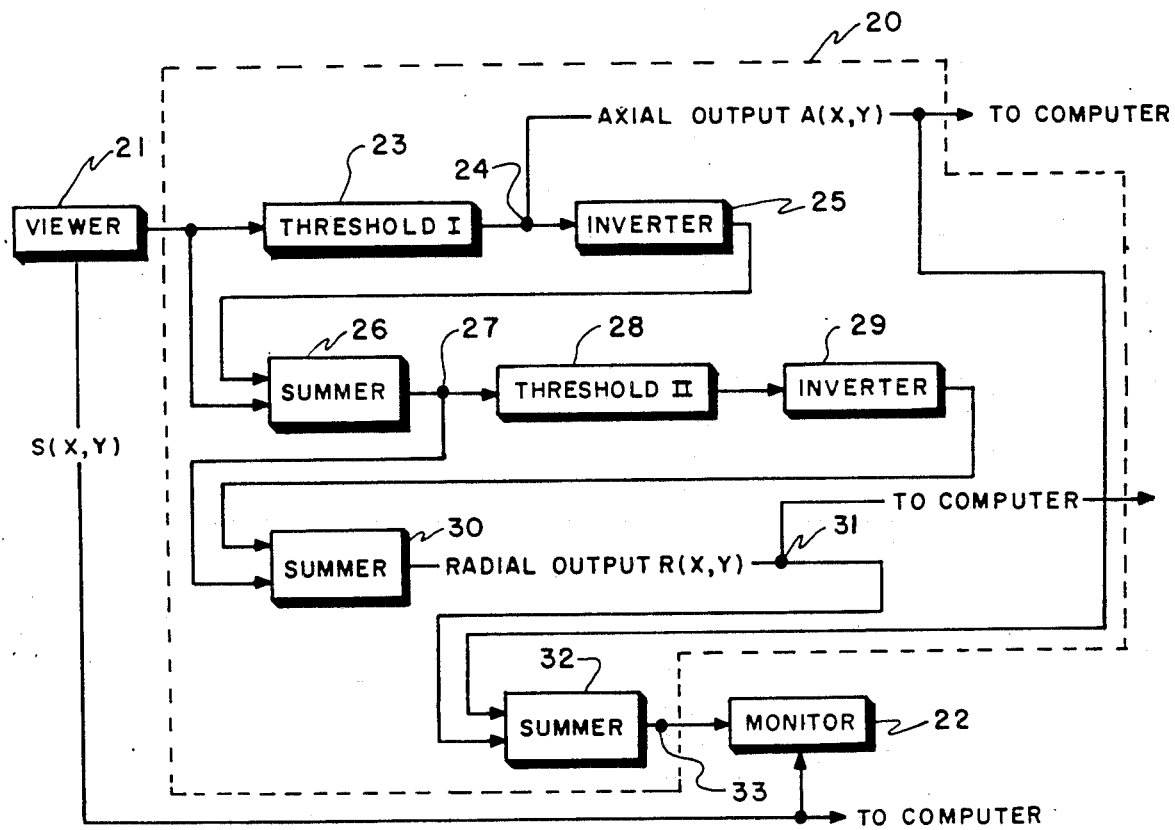
FIG. 2 shows an analog threshold processing circuit unit which is used with the FIG. 1 signal as an input.

Referring to FIG. 2, there is shown a block diagram of an analog processing circuit 20 for use with the input signal depicted in FIG. 1. Viewer 21 produces the input video cathode ray tube (CRT) type. The pulsed video signal first passes through the axial threshold circuit 23 which passes only the portions of the pulses in FIG. 1 which lie above level THRESHOLD I and preferably restores tham to at least their original amplitude. The resultant axial pulses at axial terminal 24 are ready for computer input, but they are also inverted in circuit elements 29 and fed to one input of axial summer 26. The original output of the viewer is also fed into a second input of this summer so that the output at terminal 27 lacks the axial pulses, which exactly cancel out or become negative and are unable to pass through the polarized output elements of the summer. The output from terminal 27 is passed through the radial threshold circuit 28, inverter 29 and fed to one input of the radial 30. Combined with the signal from terminal 27 which is connected to a second input of summer 30 the input signals produce a radial output at radial terminal 31 which lacks any remaining pulses above the radial threshold (THRESHOLD II in FIG. 1). The signals from the axial and radial output terminals are then fed to separate inputs of a monitor summer 32 creating a monitor video input signal at terminal 33 which can then be connected to the input of monitor 22. Threshold or limiter circuits with adjustable levels, per se, are old in the art, as are summers. All summer do not have polarized outputs as required herein, but this is easily remedied by using a diode to couple such summers to output terminals 27 and 31.

Referring again to FIG. 1 it can be seen that someone looking at the monitor can begin with both thresholds at zero and raise the level of the axial threshold until only the brightest areas defining the subjects joints are seen and these are reduced to only a few pixel pulses such as $P_0$ and $P_1$. The radial pulses are then admitted to the monitor screen by raising the level of THRESHOLD II. This level is raised only high enough to admit a limited number pixels pulses, such as $P_6$, $P_7$, $P_8$ and $P_9$, between every pair of joints that define a portion of the subjects body therebetween. The radial pulses can be amplified to a uniform high brightness level by summer 30, if desired, but their lower intensity can be a useful distinguishing feature to an observer. Pixel pulses such as $P_2$, $P_3$, $P_4$ and $P_5$ which may constitute more than 90% of the pixel pulses from the viewer are discarded.

Figure 3:
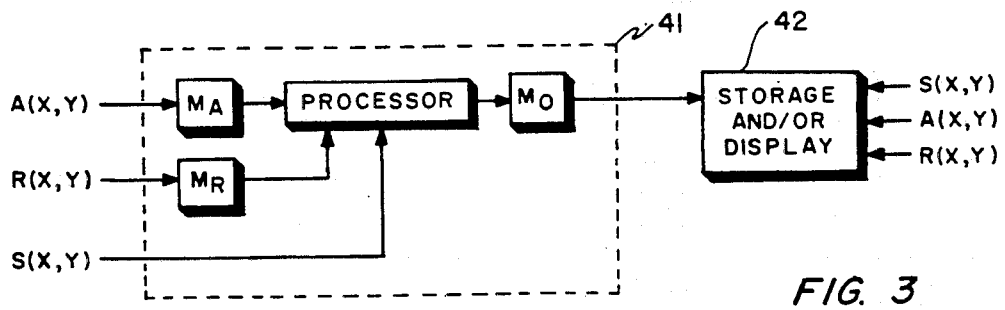
FIG. 3 shows an additional processing unit with a preprogrammed computer for processing the output signals from the circuit of FIG. 2.

FIG. 3 shows a block diagram of the digital processing circuits that can be used with the present invention. The process could conclude with the presentation of data on monitor 22 in FIG. 2. However, it will usually be beneficial to record the results in a storage device 42 with or without a display such as monitor 22. The axial and radial outputs and the synchronization signals can be directly input and recorded on video tape for example. A preferred method, however, is to first refine these signals with a digital computer 41. The digital computer stores the paired x and y coordinates of axial and radial pulses in different sections of memory, designated MA and MR, respectively. Since the intensity of the pulses is no longer a necessary characteristic the pulses can be stored in digital storage registers as bits, the order of the register and bit position therein denoting its x and y values.

The computer first sorts the axial pixels into basic groups where neither x nor y differs by more than s from another pixel in the group, s being a value from zero to about 5. An average value of x and y are determined and a centroidal pixel having these values is stored in a third section of memory Mo. As each centroidal pixel is recorded the basic group of pixels can be erased freeing up their memory registers in Ma. As soon as at least one pair of centroidal pixels are available the computer can compute the total number and the x and y values of synthetic stick pixels which represent the straight line segment between the pair and compares them with the stored x and y values of the radial pixels. If both the x and the y comparisons produce differences less than r then a radial pixel counter is incremented, r being a value between 0 and 5. The total number stick pixels is then compared to the number of radial pixels counted to justify recording the former. For example, if r=0 the maximum possible radial pixel count equals the number of stick pixels. Since there is some likelihood that a cool spot might appear on the subject's arm, for example, the decision to enter this group of stick pixels is based on less than 100% of the maximum. A high percentage is preferred, however, to exclude sticks between the subjects elbows, for example, due to a large number of intervening pixels from the trunk of his body. When a favorable decision is made the stick pixels are stored in $M_0$. This is repeated for every different pair of centroidal pixels. Since the data is output in video format the occasional appearance of a flase stick may be acceptable. Other values of r may lead to better decisions under special circumstances such as body build, clothing or the type physical activity.

A completely computerized process for obtaining a stick figure from a signal as depicted in FIG. 1 is disclosed in U.S. Pat. No. 4,539,704 for an "Image Thinning Process" issued on Sept. 2, 1985 to Jose Pastor. Once the basic data on the stick figures is established it is a simple matter for a skilled programmer to expand or shrink it and otherwise enhance it by further processing.

I claim:

1. The method of recording the movements of a human subject engaged in physical activity comprising the steps of:
   detecting the far-infrared image of said subject at less than one-tenth second intervals in the format of electronic pixel signals of varying amplitude identified with one of y rows and one of x columns in said image; and
   thinning said image to a stick figure.

2. The method according to claim 1 wherein said step of thinning said image comprises the steps of:
   separating axial pixels which have an amplitude above an axial threshold from radial pixels of lesser amplitude above a radial threshold;
   further separating said axial pixels into axial groups wherein neither the row nor the column difference between any pixel and at least one other pixel in the same group is greater than s, where s has a value between zero and five;
   electronically recording, for each axial group, a centroidal pixel with special values of x and y approximating the average x and y positions for all the pixels in said axial group, so as to define a plurality of centroidal pixels;
   computing from said special values for every pair of said centroidal pixels sets of stick pixels, each of which represents a straight line between a different pair of said centroidal pixels;
   further separating said radial pixels into radial groups, all pixels of each group being within a few pixel widths of the same one of said sets of stick pixels; and
   electronically recording said sets of stick pixels having more than R pixels, where R has a value between 1 and 25.

3. The method according to claim 2 further including the step of:
   electronically recording all possible pixel positions within a pixel of said centroidal pixels.

4. The method according to claim 3 wherein:
   said x and y positions are recorded in ascending order of x and y.

5. The method according to claim 3 further comprising the step of:
   displaying all of the pixels on a monitor for which x and y positions have been recorded.

6. The method according to claim 4 further comprising the step of:
   displaying all of the pixels on a monitor for which x and y positions have been recorded.

7. The method according to claim 2, wherein:
   5=1.

* * * * *